United States Patent
Matsumura et al.

(10) Patent No.: US 11,412,991 B2
(45) Date of Patent: Aug. 16, 2022

(54) SENSOR DEVICE AND MONITORING SYSTEM

(71) Applicant: NIHON KOHDEN CORPORATION, Tokyo (JP)

(72) Inventors: Fumiyuki Matsumura, Tokyo (JP); Norihito Konno, Tokyo (JP); Hirohiko Ikeya, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 84 days.

(21) Appl. No.: 15/877,155

(22) Filed: Jan. 22, 2018

(65) Prior Publication Data

US 2018/0228445 A1 Aug. 16, 2018

(30) Foreign Application Priority Data

Feb. 16, 2017 (JP) .............................. JP2017-026611

(51) Int. Cl.
*A61B 5/00* (2006.01)
*A61B 5/024* (2006.01)
(Continued)

(52) U.S. Cl.
CPC .......... *A61B 5/7275* (2013.01); *A61B 5/0006* (2013.01); *A61B 5/0008* (2013.01);
(Continued)

(58) Field of Classification Search
None
See application file for complete search history.

(56) References Cited

U.S. PATENT DOCUMENTS 4,865,044 A * 9/1989 Wallace ................... G01K 3/14
                                                      374/E1.004
5,228,449 A * 7/1993 Christ ................ A61B 5/02438
                                                      600/504
(Continued)

FOREIGN PATENT DOCUMENTS

JP     H01255097 A    10/1989
JP     H11128174 A     5/1999
(Continued)

OTHER PUBLICATIONS

Tokai Bureau of Telecommunications "Research and Examination of Mobile Wireless Communication System Applying Multi-Hop Sensor Network Technology" (machine English Translation), Ministry of Internal Affairs and Communications (Aug. 27, 2013), http://www.soumu.go.jp/soutsu/tokai/kohosiryo/25/0827-1.html, 6.

(Continued)

*Primary Examiner* — Carl H Layno
*Assistant Examiner* — Manolis Pahakis
(74) *Attorney, Agent, or Firm* — Dorsey & Whitney LLP (57) ABSTRACT

A monitoring system monitoring health conditions of multiple many users wearing sensor devices. Each of the sensor devices includes a first measurement section attached to a user and measuring first biological information of the user, a storage section storing information for identifying the user, an analysis section analyzing a measurement result of the first measurement section to determine that the measurement result matches with a first condition and a communication section transmitting a determination result indicating the match with the first condition received from the analysis section and information for identifying the user to communication devices located at equal intervals.

11 Claims, 3 Drawing Sheets

(51) Int. Cl.
*G16H 40/63* (2018.01)
*G16H 50/20* (2018.01)
*G16H 40/67* (2018.01)
*G08B 21/04* (2006.01)
*A61B 5/145* (2006.01)
*A61B 5/0205* (2006.01)
*A61B 5/316* (2021.01)

(52) U.S. Cl.
CPC .......... *A61B 5/02438* (2013.01); *A61B 5/742* (2013.01); *G16H 40/63* (2018.01); *G16H 40/67* (2018.01); *G16H 50/20* (2018.01); *A61B 5/02055* (2013.01); *A61B 5/14532* (2013.01); *A61B 5/316* (2021.01); *G08B 21/0453* (2013.01)

(56) References Cited

U.S. PATENT DOCUMENTS

| | | | | |
|---|---|---|---|---|
| 5,638,824 | A * | 6/1997 | Summers | G01S 15/523 600/534 |
| 5,873,369 | A * | 2/1999 | Laniado | A61B 5/0002 600/300 |
| 6,364,834 | B1 * | 4/2002 | Reuss | G16H 80/00 600/300 |
| 8,112,151 | B1 * | 2/2012 | Cogan | A61N 1/37258 607/32 |
| 8,421,606 | B2 * | 4/2013 | Collins, Jr. | A61G 7/015 340/286.07 |
| 9,643,722 | B1 * | 5/2017 | Myslinski | H04N 7/183 |
| 2002/0010390 | A1 * | 1/2002 | Guice | G16H 50/20 600/300 |
| 2003/0092971 | A1 * | 5/2003 | Intrator | G16H 40/67 128/903 |
| 2004/0074448 | A1 * | 4/2004 | Bunt | A01K 11/006 119/421 |
| 2005/0075542 | A1 * | 4/2005 | Goldreich | A61B 5/6887 600/300 |
| 2007/0043304 | A1 * | 2/2007 | Katayama | A61B 5/411 128/903 |
| 2007/0179540 | A1 * | 8/2007 | Stegemann | A61N 1/39622 607/5 |
| 2007/0197878 | A1 * | 8/2007 | Shklarski | H04L 67/04 600/300 |
| 2007/0214046 | A1 * | 9/2007 | Falchuk | G06Q 10/06 705/14.42 |
| 2007/0225611 | A1 * | 9/2007 | Kumar | A61B 5/25 600/523 |
| 2007/0287923 | A1 * | 12/2007 | Adkins | A61B 5/02405 600/485 |
| 2008/0001735 | A1 * | 1/2008 | Tran | G06F 19/00 340/539.22 |
| 2008/0004904 | A1 * | 1/2008 | Tran | A61B 5/0006 705/2 |
| 2008/0045806 | A1 * | 2/2008 | Keppler | A61B 5/1172 600/300 |
| 2008/0077326 | A1 * | 3/2008 | Funk | G01C 21/165 701/500 |
| 2008/0164979 | A1 * | 7/2008 | Otto | A61B 5/0002 340/286.01 |
| 2008/0243879 | A1 * | 10/2008 | Gokhale | G06F 3/067 |
| 2008/0266118 | A1 * | 10/2008 | Pierson | A61B 5/0205 340/573.6 |
| 2008/0288027 | A1 * | 11/2008 | Kroll | A61B 5/076 340/572.1 |
| 2009/0069642 | A1 * | 3/2009 | Gao | A61B 5/02055 600/300 |
| 2010/0112536 | A1 * | 5/2010 | Claassen | A63B 24/0075 434/258 |
| 2010/0274100 | A1 | 10/2010 | Behar et al. | |
| 2010/0317420 | A1 * | 12/2010 | Hoffberg | G06Q 30/0282 463/1 |
| 2011/0032103 | A1 * | 2/2011 | Bhat | G08B 21/02 348/143 |
| 2011/0166464 | A1 * | 7/2011 | Lee | A61N 1/37288 600/509 |
| 2012/0232416 | A1 * | 9/2012 | Gilham | G16H 40/63 600/515 |
| 2012/0315862 | A1 | 12/2012 | Okano | |
| 2013/0019408 | A1 * | 1/2013 | Jacofsky | A61B 5/447 5/613 |
| 2013/0096649 | A1 * | 4/2013 | Martin | G06F 19/3418 607/60 |
| 2013/0332201 | A1 * | 12/2013 | Hagelstein | G06Q 40/08 705/4 |
| 2014/0091811 | A1 * | 4/2014 | Potyrailo | G06K 19/0717 324/602 |
| 2014/0094136 | A1 * | 4/2014 | Huang | G01S 1/04 455/404.2 |
| 2014/0095102 | A1 * | 4/2014 | Potyrailo | G01R 27/28 702/127 |
| 2014/0142448 | A1 * | 5/2014 | Bae | A61B 5/349 600/515 |
| 2015/0018660 | A1 * | 1/2015 | Thomson | A61B 5/332 600/393 |
| 2015/0065816 | A1 * | 3/2015 | Harrison | A61B 5/14551 600/301 |
| 2015/0077245 | A1 * | 3/2015 | Kaufman | A61B 5/14551 340/539.12 |
| 2015/0164351 | A1 * | 6/2015 | He | A61B 5/1102 702/19 |
| 2015/0164377 | A1 * | 6/2015 | Nathan | A61B 5/6802 600/595 |
| 2015/0170495 | A1 * | 6/2015 | Van Oorschot | A61F 5/56 340/573.7 |
| 2015/0265903 | A1 * | 9/2015 | Kolen | G06Q 10/06398 700/91 |
| 2015/0302057 | A1 * | 10/2015 | Kealey | H04L 9/30 707/768 |
| 2015/0363280 | A1 * | 12/2015 | Yeager | A61B 5/00 711/104 |
| 2016/0070121 | A1 * | 3/2016 | Sales | A61B 7/04 351/158 |
| 2016/0120433 | A1 * | 5/2016 | Hughes | A61B 5/0022 600/483 |
| 2016/0235314 | A1 * | 8/2016 | Tsai | A61B 7/04 |
| 2016/0296176 | A1 * | 10/2016 | Mu | A61B 5/6829 |
| 2016/0302677 | A1 * | 10/2016 | He | A61B 5/02125 |
| 2017/0020399 | A1 * | 1/2017 | Shemesh | A61B 5/0205 |
| 2017/0024451 | A1 * | 1/2017 | Sullivan | G06F 16/273 |
| 2017/0188895 | A1 * | 7/2017 | Nathan | A61B 5/1118 |
| 2017/0296052 | A1 | 10/2017 | Behar et al. | |
| 2017/0311903 | A1 * | 11/2017 | Davis | G16H 40/67 |
| 2018/0027473 | A1 * | 1/2018 | Kalogridis | H04L 12/1457 370/235 |
| 2020/0100693 | A1 * | 4/2020 | Velo | G16H 40/63 |
| 2021/0223817 | A1 * | 7/2021 | Ishii | G06F 3/016 |

FOREIGN PATENT DOCUMENTS

| | | |
|---|---|---|
| JP | H11206721 A | 8/1999 |
| JP | 2006110180 A | 4/2006 |
| JP | 2008047097 A | 2/2008 |
| JP | 2008503268 A | 2/2008 |
| JP | 2012254120 A | 12/2012 |
| JP | 5237509 B1 | 4/2013 |
| JP | 2015142335 A | 8/2015 |
| JP | 2016059770 A | 4/2016 |
| JP | 2016135172 A | 7/2016 |

OTHER PUBLICATIONS

English translation of Notice of Reasons for Refusal for JP Application No. 2017-026611, dated Jan. 19, 2021.

English translation of Notice of Reasons for Refusal for JP Application No. 2017-026611, dated Sep. 23, 2020.

Oguri, Koji , "920MHz band multi-hop sensor network technology survey and examination of applied mobile wireless communication (56) References Cited

OTHER PUBLICATIONS systems", National Diet Library Internet Reference Collection Preservation Enterprise, https://warp.da.ndl.go.jp/info:ndljp/pid/8658551/www.soumu.go.jp/main_content/000283687.pdf, published Mar. 2014, partial English translation.

* cited by examiner

SENSOR DEVICE AND MONITORING SYSTEM

This application claims the benefit under 35 U.S.C. § 119 of the earlier filing date of Japanese Application No. 2017-026611 filed Feb. 16, 2017. The priority Japanese application is hereby incorporated by reference in its entirety for any purpose.

TECHNICAL FIELD

The present disclosure relates to a sensor device and a monitoring system for suitably monitoring and watching health conditions of users by many sensor devices.

BACKGROUND

There have been runners getting injured or becoming ill at marathon races in various places.

In order to address such injuries or illness of runners in marathon races, researches of using a multi-hop sensor network among moving wireless communication devices are being made for a purpose of managing body data of runners.

However, for example, when all runners wear multi-hop sensors in a full marathon race in a scale of 20,000 entries, data of 20,000 runners will be transmitted and a data amount will be huge. Furthermore, it is difficult to predict where in a marathon course health conditions of runners get worse, therefore, detection results of all runners are constantly transmitted and data processing is hardly attainable as communication quantity is enormous, as a result, it is difficult to continuously watch the health conditions of all runners.

SUMMARY

An object of the present disclosure is to provide a sensor device and a monitoring system for suitably monitoring and watching health conditions of users of man sensor devices such as all runners of a large-scale marathon.

A sensor device according to the present disclosure includes a first measurement section attached to a user and measuring first biological information of the user, a storage section storing information for identifying the user, an analysis section analyzing a measurement result of the first measurement section to determine that the measurement result matches with a first condition and a communication section transmitting a determination result indicating the match with the first condition received from the analysis section and information for identifying the user to a communication device arranged at each fixed section.

According to the above configuration, the communication section transmits the determination result when there is the determination result indicating the match with the first condition and does not transmit the determination result when the determination result does not match with the first condition. As a result, a data amount transmitted from the communication section is largely reduced, therefore, users matching with the first condition can be positively identified and health conditions of all users of the sensor devices can be accurately grasped.

A monitoring system according to the present disclosure includes the sensor device, the communication device receiving the determination result indicating the match with at least the first condition and information for identifying the user from the communication section and a centralized control device receiving information received by the communication device from the communication device and displaying the information on a display device.

According to the above configuration, the contents of the determination result received by the communication device are checked by the display device of the centralized control device, thereby identifying the user having a disorder and grasping the disorder occurring in the user.

According to the present disclosure, it is possible to provide the sensor device and the monitoring system for suitably monitoring and watching health conditions of all many users using the sensor devices such as all runners of a large-scale marathon and the like.

DETAILED DESCRIPTION

Hereinafter, a sensor device and a monitoring system for monitoring according to an embodiment of the present disclosure will be explained with reference to the drawings.

A monitoring system is a system that monitors and watches health conditions of all users of sensor devices by reducing a transmission data amount while constantly measuring biological information and so on of all many users using the sensor devices.

Figure 1:
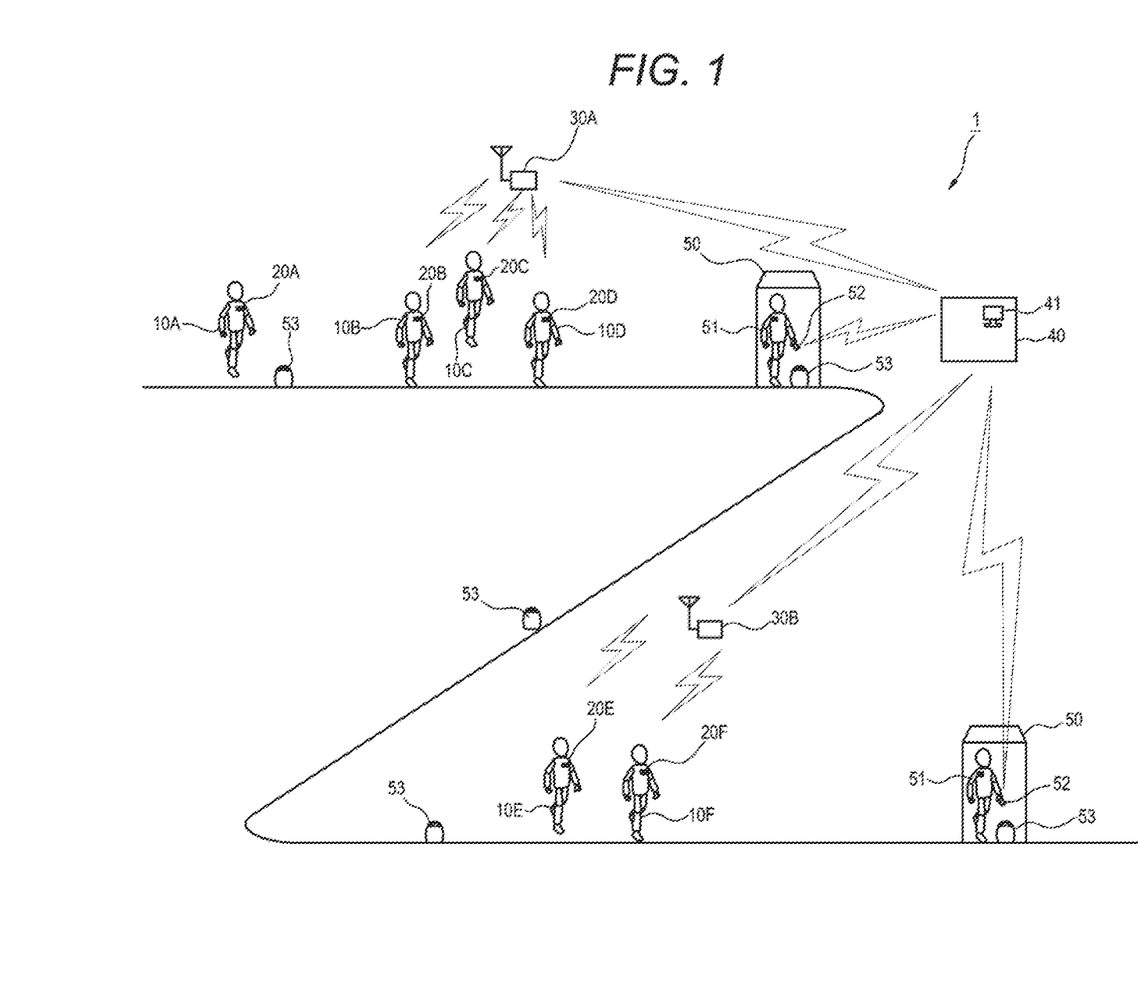
FIG. 1 is an explanatory view showing an outline of a monitoring system according to an embodiment of the present disclosure.
Figure 2:
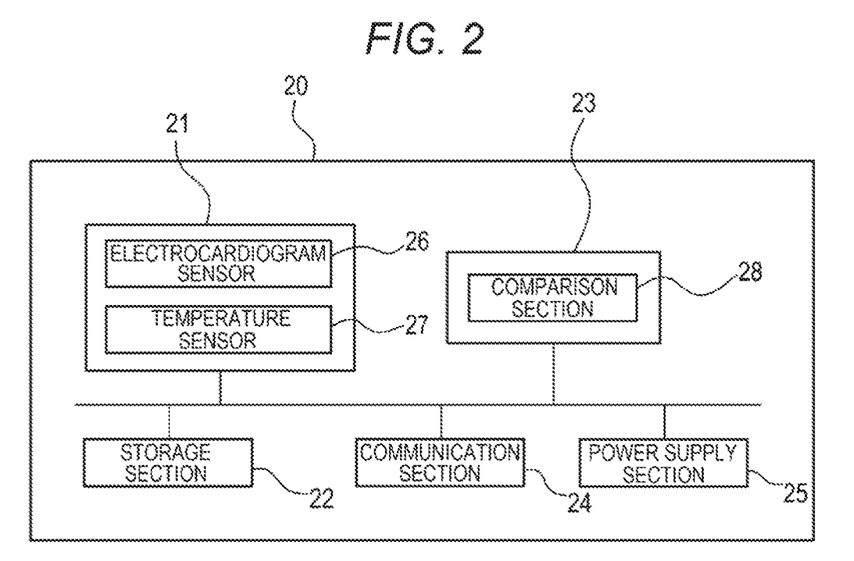
FIG. 2 is a functional block diagram of a sensor device.

FIG. 1 is an explanatory view showing an outline of a monitoring system 1 and FIG. 2 is a functional block diagram of a sensor device 20.

As shown in FIG. 1, the monitoring system 1 includes sensor devices 20A, 20B . . . , 20N attached to users 10A, 10B, . . . 10N, communication devices 30A, 30B . . . , 30N receiving information concerning users 10 from the sensor devices 20 and a centralized control device 40 controlling information received from communication devices 30 in a centralized manner. Hereinafter, when all the plural users are indicated, they are referred to as merely the "users 10", when all the sensor devices attached to respective users are indicated, they are referred to as merely the "sensor devices 20" and when all the communication devices installed in respective constant sections are indicated, they are referred to as the "communication devices 30".

An application range of the monitoring system 1 is the entire area of a course of a marathon race as an example. In this case, FIG. 1 conceptually shows the entire area of the course of the marathon race. In FIG. 1, the users 10 as marathon runners running on the marathon course, the sensor devices 20 worn by the respective users 10, the plurality of communication devices 30 provided at part of the marathon course, one centralized control device 40 installed at a marathon finish line, a plurality of first-aid stations 50 installed in the marathon course and AEDs (Automated External Defibrillators) 53 installed at the first-aid stations 50 and at plural places in the marathon course.

The monitoring system 1 can suitably monitor and watch health conditions of the users of the many sensor devices at, for example, various public transportations such as railway stations and airports, and various places/regions such as respective workplaces and so on.

In a case where the monitoring system 1 is introduced to an. enterprise to which many employees belong, an application range of the monitoring system 1 may be the entire area of a moving range and a staying range of the users 10 as employees. More specifically, the entire area which are homes, commuting routes including lines of commuter trains, workplaces such as a head office and branch offices, outing destinations and so on of the users 10. In this case, FIG. 1 shows a plurality of employees 10 of an enterprise to which the monitoring system 1 is applied, the sensor devices 20 worn by the respective employees 10, the communication devices 30 installed at a side entrance of the enterprise, ticket gates of railway stations and so on, the centralized control device 40 installed at a medical office or the like of the enterprise, the first-aid stations 50 at railway stations and so on and the AEDs 53 installed at the first-aid stations 50, ticket gates of the stations and so on.

<Sensor Device>

The sensor device 20 is a sensor attached to the user 10 as a monitoring target as shown in FIG. 1. The sensor device 20 includes a measurement section 21, a storage section 22, an analysis section 23, a communication section 24 and a power supply section 25 as shown in FIG. 2.

<Measurement Section>

The measurement section 21 is configured to be able to measure biological information of the users 10 and information concerning the measurement through electrodes or sensor terminals.

The biological information measured by the measurement section 21 is at least one of various biological information used for analysis of health conditions of the user 10. The biological information includes an electrocardiogram, a heart rate, impedance respiration, thermistor respiration, a pulse, arterial oxygen saturation, a sugar level, a cardiac output, brain waves, an electromyogram, a skin temperature, a deep body temperature, a perspiration amount, expiration carbon dioxide partial pressure and so on as examples.

Information concerning measurement is various information concerning health conditions of the users, which includes measurement start time, measurement end time, measurement time, measured positional information, movement speed, existence of falling, rotation speed of legs, ambient temperature and so on as examples.

The measurement section 21 may be configured to include a first measurement section capable of measuring first biological information a the user 10 and information concerning measurement. The first biological information is at least any one of information in the biological information. The first measuring section can be an electrocardiogram sensor 26 that measures an electrocardiogram of the user 10 as shown in FIG. 2 as an example.

The measurement section 21 is configured to generate a measurement result signal in which a measurement result of biological information and information concerning measurement are associated with each other. The measurement result signal is generated so that a determination result indicating occurrence of arrhythmia, positional information of the user at a time when arrhythmia is measured and a measurement start time of arrhythmia are associated to one another. The first measurement section can configured to generate the measurement result signal in which a measurement result of the first biological information and information concerning measurement are associated with each other instead of the measurement section 21 or in addition to the measurement section 21.

The measurement result signal Reiterated by the measurement section 21 or the first measurement section is transmitted to the storage section 22 and the communication section 24.

A configuration of the measurement section 21 is not limited to the electrocardiogram sensor 26 (first measurement section), and various types of configurations capable of measuring biological information and so on of the user 10 may be adopted. As an example, the measurement section 21 can be configured to include a second measurement section that measures information concerning second biological information of the user 10 and information concerning measurement in addition to the first measurement section or instead of the first measurement section.

The second biological information is at least any one of information other than the first biological information in the biological information. As an example, when the first biological information is an electrocardiogram, the second biological information may be a body temperature such as a skin temperature or a deep body temperature. When the second biological information is the body temperature, the second measurement section may be a temperature sensor 27. In FIG. 2, the sensor device 20 including the temperature sensor 27 as one example of the second measurement section is shown in addition to the electrocardiogram sensor 26 as one example of the first measurement section.

When the second biological information is measured, the second measurement section is configured to generate the measurement result signal in which a measurement result of the second biological information and information concerning measurement are associated with each other.

<Storage Section>

The storage section 22 is configured to store various types of information concerning the user 10. The storage section 22 is configured to stare at least three types of information.

The storage section 22 is firstly configured to stare information for identifying the user 10.

Information for identifying the user 10 includes identification information for identifying the sensor device 20 such as an ID (Identification) and the like of the sensor device 20, information for identifying each user 10 by giving an individual ID such as a number or the like to the user 10 and so on.

The storage section 22 is secondly configured to previously store information used for comparison by the analysis section 23.

Information used for comparison by the analysis section 23 includes analysis pattern information as a first condition, analysis pattern information as a second condition and analysis pattern information concerning emergency. The storage section 22 stores the analysis pattern information as the first condition and the analysis pattern information concerning emergency in these analysis pattern information. The analysis pattern as the second condition is stored in the analysis section 23.

The storage section 22 is configured to store plural types a analysis pattern information as the first condition in advance. The analysis pattern information as the first condition is, for example, names of arrhythmia, a case of an electrocardiogram waveform of arrhythmia not having emergency but haying necessity of monitoring, a value of an extremely frequent pulse detected when arrhythmia is generated and so on.

The storage section 22 is configured so as to store plural types of analysis pattern information concerning emergency. The analysis pattern information concerning emergency is, for example, the electrocardiogram waveform which should be determined as a state where the emergency is high and the AED 53 is required to be used immediately.

The storage section 22 is thirdly configured to store actual measurement results, various types of determination results concerning the measurement results and measurement result signals.

Specifically, the storage section 22 is configured to store at least one of the measurement result of biological information measured by the measurement section 21, the measurement result of the first biological information measured by the first measurement section and the measurement result of the second biological information measured by the second measurement section as actual measurement results. The storage section 22 may be configured to store all the actual measurement results as well as may be configured to store part of the actual measurement results. The actual measurement results are, for example, all electrocardiogram waveforms constantly measured at all sections to which the monitoring system 1 is applied in the marathon course or the like.

The storage section 22 is configured to store a determination result indicating a match with the first condition and a determination result indicating a match with the second condition as various types of determination results concerning measurement results.

The storage section 22 is also configured to store a determination result indicating that the measurement result matches with the analysis pattern information concerning emergency.

<Analysis Section>

The analysis section 23 is configured to determine that the measurement result matches with the first condition or the second condition by analyzing the measurement result obtained by at least any one of the measurement section 21, the first measurement section and the second measurement section.

As shown in FIG. 2, the analysis section 23 may be configured to include a comparison section 28. The comparison section 28 is configured to determine whether the measurement result of the measurement section 21 matches with analysis pattern information of the first condition or the second condition by comparing them and to determine that the result matches with the first condition or the second condition when they match with each other.

The analysis section 23 is also configured to determine that the measurement result of the first measurement section matches with the first condition by analyzing the measurement result.

The comparison section 28 in the analysis section 23 shown in FIG. 2 is configured to determine whether the measurement result of the first measurement section matches with analysis pattern information of the first condition by comparing them and to determine that the measurement result matches with the first condition when they match with each other.

The analysis section 23 is configured to store analysis pattern information as the second condition. The analysis pattern information as the second condition includes threshold values of body temperature (skin temperature, deep body temperature), a variation pattern indicating that the temperature varies excessively and so on as examples.

The analysis section 23 is configured to analyze the measurement result of the second measurement section and to determine whether the measurement result matches with the second condition. That is, the comparison section 28 is configured to determine whether the measurement result of the second measurement section matches with analysis pattern information of the second condition by comparing them and to determine that the result matches with the second condition when they match with each other.

The analysis section 23 is also configured to determine whether the measurement result matches with the analysis pattern concerning emergency. That is, the analysis section 23 reads the analysis pattern concerning emergency from the storage section 22 and determines whether the measurement result matches with the analysis pattern information concerning emergency by comparing them, then, generates a signal concerning emergency when the measurement result matches with the analysis pattern concerning emergency.

The analysis section 23 is configured to transmit the determination result to the storage section 22 and the communication section 24 when the analysis section 23 determines that the determination result matches with any one of the first condition and the second condition.

The analysis section 23 is also configured to transmit the determination result to the storage section 22 and the communication section 24 when the analysis section 23 determines that the determination result matches with the analysis pattern concerning emergency.

When it is determined that any one of measurement results of the measurement section 21, the first measurement section and the second measurement section does not match with any of analysis patterns of the first condition and the section condition and the analysis pattern concerning emergency, the storage section 22 may be configured not to store the determination result. According to such configuration, the storage capacity of the storage section 22 can be utilized at the maximum.

<Communication Section>

The communication section 24 is configured to receive information concerning the user 10 from the storage section 22 when receiving the determination result indicating the match with the first condition or the second condition from the analysis section 23. The communication section 24 is configured to store the determination result indicating the match with the first condition of the second condition received from the analysis section 23 and the measurement result signal received from at least any one of the first measurement section and the second measurement section so as to be associated with each other. The communication section 24 is configured to transmit information concerning the user 10 and information in which the determination result indicating the match with the first condition or the second condition is associated with the measurement result signal to the communication device 30.

When the communication device 30 does not exist in a range where the transmission can, be performed by the communication section 24, the communication section 24 is configured to hold various signals to be transmitted until the communication device 30 enters the range where the transmission is possible.

When the communication section 24 receives a signal concerning emergency, the communication section 24 is configured to transmit the signal concerning emergency and information for identifying the user 10 immediately.

The communication section 24 receiving the signal concerning emergency is configured to mutually communicate with the communication section 24 of another user 10. That is, the communication section 24 not only has the normal transmission function matching with the first condition or the second condition but also functions as a transfer medium that transfers the signal concerning emergency. The communication section 24 of the sensor device 20B is configured to transmit the signal concerning emergency of the user 10A to the nearest communication devices 30A, ..., 30N and to transmit the signal concerning emergency of the user 10A to the communication sections 24 of other users 10C, ..., 10N at the same time.

<Power Supply Section>

The power supply section 25 is configured to supply power necessary for respective operations of the measurement section 21, the storage section 22, the analysis section 23, the communication section 24, the electrocardiogram sensor 26 and the temperature sensor 27 shown in FIG. 2.

<First-Aid Station and Mobile Terminal>

The first-aid stations 50 can be provided in the monitoring system 1 as shown in FIG. 1. The first-aid stations 50 are provided in a marathon course of a marathon race, various public transportations such as railway stations and airports, companies having many employees and 60 on.

In the first-aid stations 50, rescuers 51 are allowed to stand by.

The rescuer 51 has a mobile terminal 52 such as a smart phone. For example, when the monitoring system 1 is applied to the marathon race, positional information of the user 10 as a marathon runner requiring a rescue, information of a number for identifying the user 10 and information of a treatment instruction and the like as rescue contents are transmitted to the mobile terminal 52.

The AEDs 53 are installed so as to be carried. at plural places such as the first-aid stations 50 and various public transportations such as platforms of railway stations. In case of emergency, the rescuer 51 can rush to a place where the user 10 requiring a rescue exists immediately with the AED 53 installed in the first-aid station 50 or the like.

<Communication Device>

The communication device 30 is configured to receive information such as the determination result indicating the match with the first condition from the communication section 24 of the sensor device 20.

The communication devices 30 are installed at respective fixed sections in a region where the user 10 as a monitoring target passes through or stays. In the case where the application range of the monitoring system 1 is the entire course of the marathon race as an example, the communication devices 30 are installed in respective plural sections into which the entire course is divided at equal intervals. In the case where the monitoring system 1 is introduced into an enterprise as an example, the communication devices 30 are installed in respective ticket gates of railway stations where the users 10 get on and off, respective bus stops of respective routes of privately-owned and metropolitan buses in a metropolitan area, respective public toilets at public institutions of public parks in the metropolitan area, elevator halls in respective floors, toilets in respective floors, an employee entrance and so on in companies having many employees.

The communication device 30 is configured to transmit information of the determination result indicating that the user 10 matches with the first condition received from the sensor device 20 and so on to the centralized control device 40.

<Centralized Control Device>

The centralized control device 40 is configured to receive information of the determination result indicating the match with the first condition and so on from plural communication devices 30. As shown in FIG. 1, the centralized control device 40 includes a display device 41 displaying information received by the centralized control device 40, Examples of the display device 41 include a tablet terminal, a personal computer screen and the like.

Here, an outline of information displayed on the display device 41 will be explained prior to explanation of information displayed on the display device 41.

Information displayed on the display device 41 includes the determination result indicating that the user 10 matches with the first condition or the second condition and so on.

The determination indicating that the user 10 matches with at least any one of the first condition and the second condition may be performed by the above-described sensor device 20 as well as may be performed by the centralized control device 40.

In the case where the centralized control device 40 determines whether the measurement result matches with the first condition or the second condition, the sensor device 20 does not determine whether the measurement result matches with the first condition or the second condition.

In this case, at least any one of the measurement section 21, the first measurement section and the second measurement section of the sensor device 20 is configured to generate a measurement result signal by associating at least any one of the biological information, the first biological information and the second biological information with information concerning measurement such as a measurement time and to transmit the measurement result signal to the storage section 22 and the communication section 24.

The communication section 24 receives information for identifying the user 10 from the storage section 22, receives the measurement result, of the biological information and the measurement result signal from the measurement section 21 and transmits the received information to the centralized control device 40 through the communication device 30.

The communication section 24 also receives information for identifying the user 10 from the storage section 22, receives the measurement result of the first biological information and the measurement result signal from the first measurement section and transmits the received information to the centralized control device 40 through the communication device 30.

The communication section 24 also receives information for identifying the user 10 from the storage section 22, receives the measurement result of the second biological information and the measurement result signal from the second measurement section and transmits the received information to the centralized control device 40 through the communication device 30.

The centralized control device 40 is configured to determine whether at least any one of the received measurement results of the measurement section 21, the first measurement section and the second measurement section matches with any one of the first condition and the second condition.

The determination result determined to match with at least any one of the first condition and the second condition by the centralized control device 40 is displayed on the display device 41. A doctor seeing the determination result displayed on the display device 41 can use the determination result for determining whether the user 10 such as a runner may continue running or not.

Figure 3:
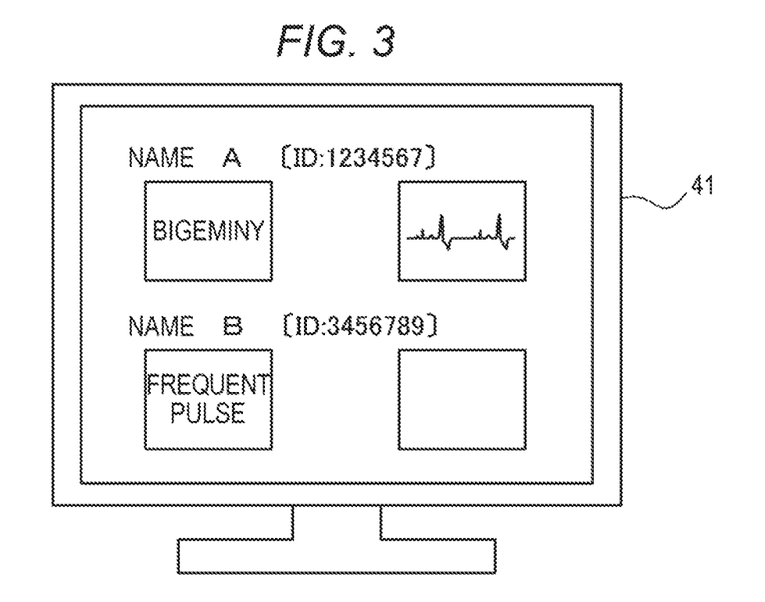
FIG. 3 is an explanatory view showing a display device.

FIG. 3 is an explanatory view showing one example of in nation displayed on the display device 41.

On an upper side of a display screen of the display device 41 of FIG. 3, a name of the user 10A, an ID of the sensor device 20 of the user 10A, a state (bigeminy) of the user 10A and a measurement result of an electrocardiogram of the user 10A are displayed. On a lower side of the display screen of the display device 41, a name of the user 10B, an ID of the sensor device 20 of the user 10B and a state (frequent pulse) of the user 10B are displayed.

The determination result determined to match with at least any one of the first condition and the second condition by the centralized control device 40 may be transmitted to the mobile terminal 52 of the rescuer 51. The rescuer 51 can check information received by the mobile terminal 52 and rescue the user 10 matching with the first condition or the second condition by holding the AED 53 installed in the first-aid station 50 or the like.

Though one centralized control device 40 is shown in FIG. 1, the number of the centralized control devices 40 is not limited to one, and a plurality of centralized control devices suitable to be used for the monitoring system 1 can be installed.

For example, when the monitoring system 1 is configured to have the communication devices 30A, 30B, . . . , 30E (not shown) as a first group of communication devices and the communication devices 30F, 30G, . . . , 30J (not shown) as a second group of communication devices, the centralized control device 40 can be configured by including a first centralized control device (not shown) receiving information from the first group of communication devices and a second centralized control device (not shown) receiving information from the second group of communication devices.

Moreover, when the monitoring system 1 is introduced into enterprises, a plurality of centralized control devices 40 can be installed at medical institutions that manage and administer the monitoring system 1 or medical offices or the like of enterprises introducing the monitoring system 1.

The centralized control device 40 may be configured to receive various types of information from the communication devices 30 through wireless communication or the like.

<Sensor Device Having Foreseeing and Prediction Section>

Figure 4:
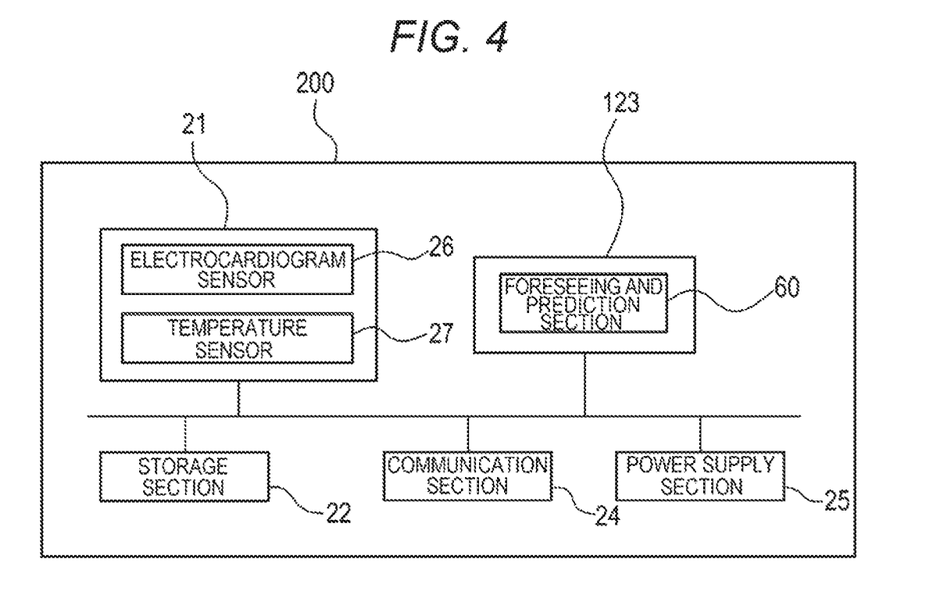
FIG. 4 is a functional block diagram of a sensor device according to a modification example.

The analysis section of the sensor device may have a configuration of including a foreseeing and prediction section 60 that determines that the user 10 matches with a third condition instead of the comparison section 28 shown in FIG. 2 or in addition to the comparison section 28 shown in FIG. 2. FIG. 4 is a block diagram showing a sensor device 200 having an analysis section 123 provided with the foreseeing and prediction section 60 instead of the comparison section shown in FIG. 2.

As the sensor device 200 has the same configuration as the sensor device 20 shown in FIG. 2 except for the analysis section 123 having the foreseeing and prediction section 60, the same symbols are given in FIG. 4 and repeated explanation is omitted.

The foreseeing and prediction section 60 is configured to determine that a slight disorder in a degree not matching with any of the first condition and the second condition is generated in the user 10 of the sensor device 200 and that there is a possibility that the slight disorder is developed into a serious disorder. Whether there is a possibility that the slight disorder of the user 10 is developed into the serious disorder is determined by whether the disorder matches with the third condition or not.

The third condition may include various types of conditions in which there is the possibility that the slight disorder occurring in the user 10 is developed into the serious disorder.

As a first example of determination of the third condition, the foreseeing and prediction section 60 may foresee and predict a state based on time elements and biological information.

The foreseeing and prediction made based on time elements and biological information include, for example, a case where the measurement result indicates the slight disorder in a degree not matching the first condition or the second condition but it is determined that there is a possibility that the slight disorder is developed into a serious disorder to match with the first condition or the second condition when the slight disorder intermittently occurs for more than a prescribed period of time.

In this first example, the third condition is that there is the possibility that the slight disorder as the measurement result is developed into the serious disorder matching with the first condition or the second condition when the slight disorder intermittently occurs for more than a prescribed period of time.

As a second example of determination of the third condition, the foreseeing and prediction section 60 may perform foreseeing and prediction by using plural biological information.

The foreseeing and prediction performed by using plural biological information correspond to, for example, a case where it is determined that plural measurement results concerning biological information indicate a slight disorder not matching with the first condition and the second condition by itself but there is a possibility that the slight disorder is developed into a serious disorder when the plural measurement results are combined.

In the second example, the third condition includes the possibility that the slight disorder not matching with the first condition and the second condition by itself is developed into the serious disorder matching with the first condition or the second condition when determination is made by the plural measurement results being combined.

As a third example of determination of the third condition, the foreseeing and prediction section 60 may perform foreseeing and prediction by using related information and biological information of the user 10.

The foreseeing and prediction performed by using related information and biological information correspond to, for example, a case where the presence of a change in information concerning the user 10 and the presence of a change in biological information of the user 10 are measured and occurrence of some change in health conditions of the user 10 is determined based on information of a sudden change occurring in one measurement result and information of no change in the other measurement result. Specifically, the foreseeing and prediction correspond to a case where the possibility of occurrence of the serious disorder is determined when there is no change in the measurement result of related information of the user 10 and a sudden change occurs in the measurement result of biological information of the user 10.

The third condition in the third example indicates that there is no change in related information of the user 10 and there is a sudden change in biological information of the user 10.

As a fourth example of determination of the third condition, the foreseeing and prediction section 60 may perform foreseeing and prediction corresponding to an individual user 10.

The foreseeing and prediction corresponding to the individual user 10 correspond to, for example, a case where determination is made that a slight disorder as a measurement result measured for the user 10 may be developed into a serious disorder in consideration of a medical history, age and the like o the user 10.

The third condition in the fourth example indicates that the measurement result matches with conditions individually set so as to correspond to individual information of the individual user 10.

The matching with the third condition includes a case where there is a probability that the user 10 matches with the first condition after a prescribed period of time passes from the measurement time of the first biological information of the user 10 in addition to the first example to the fourth example. The matching with the third condition also includes a case where there is a probability that the user 10 matches with the second condition after a prescribed period of time passes from the measurement time of the second biological information of the user 10.

When it is determined that the user matches with the third condition, the determination result is transmitted from the foreseeing and prediction section 60 to the communication section 24 of the sensor device 200. The communication section 24 may be configured to transmit the determination result indicating the match with the third condition to the centralized control device 40 through the communication device 30 as well as to directly transmit the determination result to the mobile terminal 52 of the rescuer 51.

The foreseeing and prediction section 60 is not limited to a configuration of being provided in the analysis unit 123. The foreseeing and prediction section 60 may have a configuration capable of determining whether there is a possibility that the slight disorder of the user 10 is developed into the serious disorder. For example, a configuration in which the foreseeing and prediction section 60 is included in the centralized control device 40 and the foreseeing and prediction section 60 automatically determines whether the user matches with the third condition by using the measurement result received by the centralized control device 40 from at least any one of the measurement section 21, the electrocardiogram sensor 26 (one example of the first measurement section) and the temperature sensor 27 (one example of the second measurement section) of the sensor device 200 shown in FIG. 4.

The foreseeing and prediction section 60 may have a configuration in which determination results indicating the match with the first condition or the second condition obtained in various marathon races in the past, past enormous data of measurement result signals and phenomena occurred in the past are stored to be associated with one another and determination is made by adding these determination results, data and phenomena to determination criteria of the third condition. Various phenomena occurring in the marathon race include information about dropping-out due to illness, a phenomenon that the worst health condition caused an accident and so on.

According to the configuration, the accuracy of determination indicating the match with the third condition by the foreseeing and prediction section 60 can be increased.

The past data, phenomena occurred in the data and information in which data and phenomena are associated to each other may be stored so as to be used for determination by the foreseeing and prediction section 60. The past data, phenomena occurred in the data and information in which data and phenomena are associated to each other may be, for example, stored in the analysis section 123, may be stored in the storage section 22, may be stored in the centralized control device 40, and may be stored in an external storage medium and the like which can be electrically connected to the foreseeing and prediction section 60.

Next, operation examples of the sensor devices 20, 200, the communication devices 30 and the centralized control device 40 of the monitoring system 1 will be explained.

OPERATION EXAMPLE 1

Use of Sensor Device 20 Provided with Comparison Section 28 in Marathon Race An example in which the monitoring system 1 is used for the marathon race in a scale of tens of thousands participants will be explained with reference to FIG. 1 and FIG. 2.

The application range of the monitoring system 1 is the entire area of the course of the marathon race. Each sensor device 20 is attached to each of the users 10A, 10B, 10C, . . . , 10F. The communication device 24 of the sensor device 20 of each of users 10A, . . . , 10F is configured to perform transmission within a 10 m radius. The communication device 30A is installed at a third point as a 4 km place from the start.

A case where the user 10A in FIG. 1 is positioned before the third point and arrhythmia requiring monitoring without emergency occurs in the user 10A at the position will be explained.

The occurrence of arrhythmia requiring monitoring without emergency in the user 10A is specified by the sensor device 20A of the user 10A.

That is, the electrocardiogram sensor 26 (an example of the first measurement section) of the sensor device 20A constantly measures and monitors an electrocardiogram (an example of the first biological information) of the user 10A. The electrocardiogram sensor 26 also measures the position before the third point as the position where the electrocardiogram is measured at the same time as measurement of the electrocardiogram of the user 10A. The electrocardiogram sensor 26 further measures a measurement start time when the measurement of the electrocardiogram of the user 10A is started and time concerning measurement such as a measurement period indicating how many seconds the electrocardiogram is measured. That is, the electrocardiogram sensor 26 measures positional information of the point where the electrocardiogram of the user 10A is measured, the measurement start time when the measurement of the arrhythmia is started and the measurement time indicating how many seconds the generated arrhythmia continues.

The electrocardiogram sensor 26 generates a measurement result signal by associating an electrocardiogram waveform of the user 10A as the measurement result, time concerning the measurement of the electrocardiogram waveform and positional information of the point where the electrocardiogram is measured with one another.

The measurement result signal generated by the electrocardiogram sensor 26 is transmitted to the storage section 22 and the communication section 24.

The analysis section 23 analyzes the electrocardiogram measured by the electrocardiogram sensor 26. In the analysis, the analysis section 23 receives an analysis pattern of the first condition. That is, the analysis section 23 receives an electrocardiogram waveform as the analysis pattern concerning the electrocardiogram from the storage section 22.

The comparison section 28 determines whether the electrocardiogram measured by the electrocardiogram sensor 26 corresponds to the analysis pattern received from the storage section 22 by comparing them and determines whether the measurement result matches with the first condition.

Here, when the measurement result differs from the analysis pattern of the first condition, the comparison section 28 determines that the measurement result does not match with the first condition, and does not store the determination result in the storage section 22.

In the operation example, the electrocardiogram of the user 10A has ups and downs closely resembling a waveform diagram of the electrocardiogram requiring monitoring through there is no emergency as a result of comparing the analysis pattern of the first condition with the measurement result by the comparison section 28, therefore, the comparison section 28 determines that the measurement result corresponds to the analysis pattern of the first condition. As it is determined that the measurement result corresponds to the analysis pattern of the first condition, the analysis section 23 determines that the measurement result matches with the first condition.

The determination result indicating the match with the first condition by the analysis section 23 is transmitted from the analysis section 23 to the communication section 24.

The communication section 24 of the user 10A receives information concerning the determination result when receiving the determination result indicating the match with the first condition from the analysis section 23. That is, the communication section 24 receives information for identifying the user 10A from the storage section 22 and receives the measurement result signal from the electrocardiogram sensor 26.

The communication section 24 holds the determination result indicating the match with the first condition and the measurement result signal so as to be associated with each other and holds information for identifying the user 10A.

When the user 10A is in a position where transmission can be performed to the communication device 30, the communication section 24 transmits the determination result indicating the match with the first condition, the measurement result signal and information for identifying the user 10A, which are held by the communication section 24 to the communication device 30.

In FIG. 1, the communication section 24 of the user 10A is positioned outside the transmission range to the nearest communication device 30A. Accordingly, the communication section 24 of the user 10A holds the determination result indicating the match with the first condition and the measurement result signal so as to be associated with each other and maintains a state of holding the information for identifying the user 10A.

When the user 10A comes close to the communication device 30A and the communication section 24 of the user 10A enters the range where the transmission can be performed to the communication device 30, the communication section 24 of the user 10A transmits information in which the determination result indicating the match with the first condition and the measurement result signal are associated with each other and information for identifying the user 10A to the communication device 30A.

Information transmitted from the communication section 24 of the sensor device 20A to the communication device 30A is transmitted to the centralized control device 40 through the communication device 30A.

The centralized control device 40 receives information for identifying the user 10A, the determination result indicating that the user 10A matches with the first condition and the measurement result signal from the communication device 30A and displays the information on the display device 41. The information displayed on the display device 41 is checked by a sponsor of the marathon race or medical workers standing by at the installation place of the centralized control device 40 and a suitable treatment is given.

The measurement of second biological information by the second measurement section and the determination whether the measurement result of the second biological information matches with the second condition or not are the same as the measurement of the first biological information and the determination whether the measurement result matches with the first condition in the operation example 1, therefore, explanation is omitted.

As described above, the sensor device 20 according to the present disclosure does not transmit all actual measurement results and all determination results stored in the storage section 22 to the communication device 30 without conditions. If all actual measurement results are successively transmitted from the sensor device 20 to the communication device 30 without conditions, an enormous data amount is transmitted and the communication quantity becomes huge, which delays data processing. Due to the delay in data processing, it takes time to identify the user 10 matching with the first condition or the second condition, which makes monitoring such as an immediate rescue of the user 10 difficult.

Accordingly, the sensor device 20 of the present disclosure is configured to transmit information for identifying the user 10 and the determination result indicating the match with the first condition or the second condition from the communication section 24 to the communication device 10 when the analysis section 23 determines that the determination result matches with the first condition or the second condition.

According to the configuration, information transmitted to the communication device 30 includes information for identifying the user 10 and the determination result of the user 10 indicating the match with the first condition or the second condition determined by the analysis section 23, and a data amount to be transmitted is largely reduced as compared with the case where all measurement results and the determination results are transmitted. As the data amount to be received by the communication device 30 is largely reduced, a data processing burden is reduced and identification of the user 10 in a bad condition can be performed immediately. When information of the determination result and so on received by the communication device 30 is displayed on the display device 41 of the centralized control device 40, it is possible to grasp the contents of the disorder occurring in the user 10 immediately and accurately, and appropriate treatment can be given to the user 10 in the bad condition.

It is also possible to have a configuration in which the determination result not matching with any of the first condition and the second condition is not stored in the storage section 22 of the sensor device 20. In this case, the storage capacity of the storage section 22 can be utilized at the maximum and health conditions of the user can be suitably watched.

OPERATION EXAMPLE 2

Use of Sensor Device 200 Provided With Foreseeing and Prediction Section 60 in Marathon Race>

An example in which the sensor device 200 provided with the foreseeing and prediction section 60 is used will be explained with reference to FIG. 1 and FIG. 4. Here, the foreseeing and prediction section 60 has the configuration in which foreseeing and prediction are performed based on time elements and biological information as the first example. The third condition in the operation example is a case where a slight disorder continuously occurs for 30 minutes or more and there is a possibility that the slight disorder is developed into a serious disorder. As the biological information, the electrocardiogram (one example of the first biological information) measured by the electrocardiogram sensor 26 (one example of the first measurement section) is used.

The foreseeing and prediction section 60 of the sensor device 200 reads plural measurement results of the electrocardiogram by the electrocardiogram sensor 26 stored by the storage section 22 at prescribed timing. The prescribed timing may be periodic timing such as at 10 minutes intervals as well as at timing when the user 10 passes a particular point such as timing when the user 10 passes the communication device 30.

The foreseeing and prediction section 60 analyzes a measurement result read from the storage section 22. The foreseeing and prediction section 60 determines that the measurement result matches with the third condition when the slight disorder is measured plural times intermittently in a range of the measurement time of 30 minutes or more. The determination indicating the match with the third condition is transmitted from the foreseeing and prediction section 60 to the communication section 24 with information for identifying the user 10 and transmitted to the centralized control device 40 through the communication device 30.

Information indicating the match with the third condition transmitted to the centralized control device 40 and information for identifying the user 10 are displayed on the display device 41, and suitable treatment is performed. For example, the rescuer 51 checking the display device 41 can attend the user 10 as a marathon runner who may become ill. The rescuer 51 can take an action of asking the user 10 to stop running before an emergency occurs. It is also possible to take an action of monitoring the user 10 while the rescuer 51 accompanies the user 10.

The information indicating the match with the third condition and the information for identifying the user 10 may be transmitted to the mobile terminal 52 of the rescuer 51. When the information is transmitted to the mobile terminal 52 of the rescuer 51 as described above, the rescuer 51 can take an action of preparing the AED 53 or the like while monitoring running positions of the user 10 as the marathon runner who may become ill.

As the foreseeing and prediction section 50 for determining whether the measurement result matches with the third condition is provided as described above, a sign of occurrence of a disorder of the user 10 can be detected even when the probability of a disorder such as arrhythmia is subsequently increased in the user 10 not matching with both the first condition and the second condition at the time of measurement. It is also possible to take an action of preparing the AED 53 or the like so as to correspond to the determination result indicating the match with the third condition with respect to the sign to occurrence of the disorder of the user 10. Health conditions of many users 10 can be suitably watched more properly as described above.

OPERATION EXAMPLE 3

Figure 5:
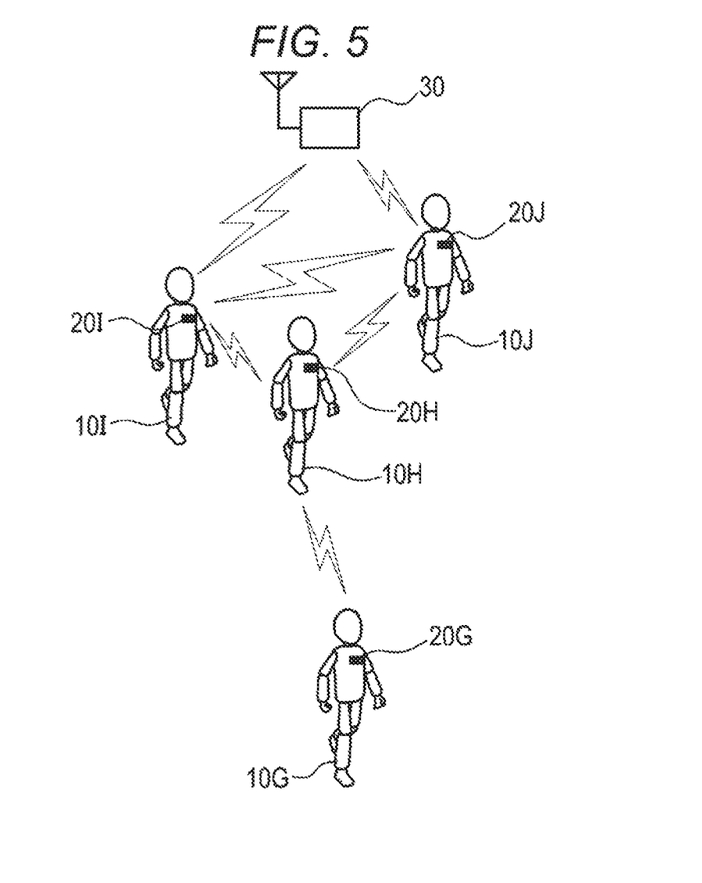
FIG. 5 is an explanatory view showing a monitoring system by a mesh network system.

Use of Monitoring System 1 Provided With Sensor Device 20 Having Communication Section 24 Used for Mesh Network System An operation example of the monitoring system 1 in which the communication sections 24 of the sensor devices 20 mutually performing communication, namely, the monitoring system 1 having a transfer function will be explained with reference to FIG. 1 to FIG. 3 and FIG. 5. FIG. 5 shows part in the course of the marathon race of FIG. 1. Arrhythmia with emergency occurs in the user 10G as a marathon runner at a 5 km point from the start.

The arrhythmia with emergency occurring in the user 10G is identified by the sensor device 20G. That is, the analysis section 23 of the sensor device 20G determines whether the user 10G matches with an analysis pattern concerning emergency or not.

The analysis section 23 of the sensor device 20G receives an electrocardiogram waveform as an analysis pattern concerning an electrocardiogram from the storage section 22 as the analysis pattern concerning emergency. The comparison section 28 of the sensor device 20G compares the electrocardiogram (an example of first biological information) measured by the electrocardiogram sensor 26 (an example of the first measurement section) with the analysis pattern concerning emergency received from the storage section 22. As it is determined that the electrocardiogram as the measurement result of the first measurement section corresponds to the electrocardiogram of the analysis pattern with emergency in the present operation example, the analysis section 23 of the sensor device 20G generates a signal concerning emergency.

The analysis section 23 of the sensor device 20G transmits a signal concerning emergency and information for identifying the user 10G to the communication section 24 of the sensor device 20G.

When the communication section 24 of the user 10G receives the signal concerning emergency from the analysis section 23, the signal concerning emergency and the information for identifying the user 10G are transmitted immediately to the circumference of both inside and outside the transmission range with respect to the communication device 30.

The communication device 30 in FIG. 5 is outside the transmission range of the communication section 24 of the sensor device 20G. The communication section 24 of the sensor device 20H is also outside the transmission range with respect to the communication device 30.

However, the communication sections 24 of other users 10I and 10J running in front of and after the user 10H are in positions in a range where transmission can be performed to the communication device 30.

Information transmitted by the communication section 24 of the sensor device 20G is not directly received by the communication device 30 but is received by the communication section 24 of the sensor device 20H of the user 10H. Information transmitted by the communication section 24 of the sensor device 20H is not directly received by the communication device 30 but is received by the communication section 24 of the sensor device 20I and the communication section 24 of the sensor device 20J.

The communication section 24 of the sensor device 20I possessed by the user 10I and the communication section 24 of the sensor device 20J possessed by the user 10J respectively transmit information for identifying the user 10G and the signal concerning emergency of the user 10G to the communication device 30.

The communication device 30 receives the information for identifying the user 10G and the signal concerning emergency of the user 10G from the communication section 24 of the sensor device 20I and the communication section 24 of the sensor device 20J and transmits them to the centralized control device 40 (see FIG. 1).

The centralized control device 40 can display the received information on the display device 41 or transmit the received information to the mobile terminal 52 of the rescuer 51, and the rescuer 51 can go to rescue the user 10G with the AED 53.

When the communication section 24 of the sensor device 20G positioned outside the transmission range with respect to the communication device 30 transmits the signal concerning emergency and the like in the monitoring system 1 according to the present disclosure as described above, the signal is transferred through the communication sections 24 of other users 10H, 10I and 10J, thereby transferring the signal concerning emergency of the user 10G to the nearest communication device 30 urgently and suitable first-aid treatment can be performed to the user 10G.

The users 10G to 10J may be in a state of a line aligned like a string as well as in a state where the users 10G to 10J are separately running while being positioned at random.

The transfer function of the communication device 24 of the sensor device 20 according to the present disclosure is not limited to application to transmission of the signal concerning emergency as shown in the operation example 3. The communication section 24 of the sensor device 20 can mutually perform communication to acquire the measurement result of the user 10 positioned outside the transmission/reception range of the communication device 30 in prescribed conditions.

Here, the prescribed conditions may include a temporal condition such as coming of time when measurement is evenly performed in the monitoring system 1 and may be a condition concerning positional information such as reaching at a temporary measurement point in the monitoring system 1.

The temporal condition may be a finish time of the marathon race in the case where the monitoring system 1 is used in the marathon race, and may be a starting time in the afternoon in the case where the monitoring system 1 is applied to an enterprise examples.

The condition concerning positional information can be positional information of the first-aid stations 50 temporarily installed at places where the communication devices 30 are not installed as an example when the monitoring system 1 is used for the marathon race. When the monitoring system 1 is applied to an enterprise, the condition can be positional information of a landing of an emergency staircase added as the measurement point only on the day of an emergency training.

The communication section 24 of the sensor device 20 positioned outside the transmission range with respect to the communication device 30 mutually performs communication with the communication section 24 of another user 10 in prescribed conditions as described above, therefore, the measurement result of the user 10 positioned outside the transmission range with respect to the communication device 30 can be urgently transferred to the nearest communication device 30, and suitable emergency treatment can be performed to the user 10.

OPERATION EXAMPLE 4

Use of Sensor Device 20 Provided With Comparison Section 28 in Monitoring System Using Public Institutions An example in which the sensor devices 20, 200 and the monitoring system 1 according to the embodiment are applied to an enterprise to which many employees belong will be explained with reference to FIG. 1 to FIG. 5.

The users 10A to 10F shown in FIG. 1 are employees of the enterprise to which the monitoring system 1 is introduced, who wear the sensor devices 20A to 20F.

The plural AEDs 53 are installed at the first-aid stations 50, various public transportations such as platforms of railway stations and the like.

The centralized control device 40 is installed at a medical institution managing and operating the monitoring system 1 or a medical office or the like of the enterprise introducing the monitoring system 1 and is configured to receive various information from the communication devices 30 through wireless communication and so on.

The sensor device 20 of the user 10 configured to perform measurement in the entire range of the measurement area and analyze measurement results. The entire range of the measurement area may be the entire range including, for example, homes, commuting routes including lines of commuter trains, workplaces such as a head office and branch offices, outing destinations and so on of the users 10.

The sensor devices 20A to 20F may be the sensor device 20 including at least the measurement section 21, the electrocardiogram sensor 26 (an example of the first measurement section) and the temperature sensor 27 (an example of the second measurement section) and the comparison section 28 or may be the sensor device 200 including at least one of the above and the foreseeing and prediction section 60 shown in FIG. 4. That is, the sensor devices 20A to 20F may be the sensor device 20 including the analysis section 23 determining that the user 10 matches with at least any one of the first condition and the second condition. The sensor devices 20A to 20F may also be the sensor device 200 including the analysis section 123 determining whether the user 10 matches with the third condition or not.

The monitoring system 1 may include the sensor devices 20A to 20F including the analysis section 23 generating the signal concerning emergency and transmitting the signal to the communication section 24 when the measurement result corresponds to analysis pattern information concerning emergency. The monitoring system 1 may have a configuration including the sensor devices 20A to 20F having the communication sections 24 performing communication with one another. The monitoring system 1 may also have a configuration of including the sensor devices 20A to 20F having the communication device 24 transmitting the signal concerning emergency to the communication device 24 of the sensor device 20 of another user 10 by the mesh network system.

These specific operations are the same as the operation examples 1 to 3, therefore, operations corresponding to the operation example 1 will be explained, and explanation of operations corresponding, to the operation examples 2 and 3 is omitted.

A case where arrhythmia without emergency occurs in the user 10A shown in FIG. 1 in a commuter train will be explained.

The arrhythmia of the user 10A is measured and analyzed by the sensor device 20A. That is, the electrocardiogram sensor 26 (an example of the first measurement section) measures an electrocardiogram of the user 10A (an example of the first biological information) and measures positional information at a point where the electrocardiogram of the user 10A is measured and information concerning the measurement such as measuring time of the electrocardiogram, and generates a measurement result signal in which the measurement result is associated with information concerning the measurement. The analysis section 23 determines that an electrocardiogram waveform measured by the electrocardiogram sensor 26 corresponds to a case of an electrocardiogram indicating the arrhythmia as analysis pattern information in the first condition by comparing the both, determining that the measurement results correspond to the first condition. The analysis section 23 transmits the determination result indicating the match with the first condition to the communication section 24.

The communication section 24 receives the determination result indicating the match with the first condition (occurrence of arrhythmia, no emergency) from the analysis section 23, receives information for identifying the user 10A from the storage section 22, receives the measurement result signal from the electrocardiogram sensor 26 to hold the signal until entering the range where transmission can be performed with respect to the communication device 30.

When the user 10A arrives at a getting-off station where the communication device 30 is installed, the communication section 24 associates the measurement result indicating the match with the first condition with the measurement result signal and transmits them to the communication device 30 with information for identifying the user 10A.

The communication device 30 transmits the received information to the centralized control device 40.

The centralized control device 40 displays the determination result indicating that the user 10A matches with the first condition on the display device 41. The rescuer 51, a doctor or the like checking the determination result displayed on the display device 41 can take an action of suitable treatment such as going to rescue the user 10 while holding the AED 53.

Also in various places/regions in various public institutes or enterprises, health conditions of many users can be suitably watched by the sensor devices and the monitoring system according to the present disclosure as described above.

The present disclosure is no limited to the above embodiment and modification examples, and modification, improvement and so on can be suitably performed. Additionally, the material, the shape, the size, numerals, the state, the number, installation places and so on of respective components in the above embodiment are arbitrary and not limited as long as the present disclosure can be achieved.

What is claimed is:

1. A sensor device comprising:
    a first biological information sensor configured to measure a first biological information of a user;
    a local storage configured to store identification information of the user;
    a communication section including a transmitter; and
    a processor coupled to the first biological information sensor and the local storage,
    wherein the sensor device is configured to be attached to the user,
    wherein the first biological information sensor, the local storage, the communication section, and the processor are housed in the sensor device, and
    wherein the processor is configured to:
        analyze a measurement result of the first biological information sensor to determine that whether the measurement result matches a first physiological condition;
        provide a determination result based on the determination of whether the measurement result matches the first physiological condition;
        responsive to the determination result indicating at least a match with the first physiological condition, the processor is further configured to:
            provide the determination result indicating at least a match with the first physiological condition to the local storage; and
            control the communication section to transmit the determination result and the identification information of the user from the local storage to a nearest one of a plurality of communication devices in communication with the sensor device; and
        responsive to the determination result indicating the measurement result does not match the first physiological condition, the processor is configured to:
            not provide the determination result to the local storage.

2. The sensor device configured to be attached to the user according to claim 1,
    wherein the first biological information sensor is configured to measure an electrocardiogram as the first biological information and generate a measurement result signal in which the measurement result is associated with information concerning measurement of the first biological information,
    the local storage is configured to store at least one of names of arrhythmia and electrocardiogram waveforms as plural types of analysis pattern information in advance, the processor is configured to compare the analysis pattern information with the measurement result and determine that the measurement result matches with the first physiological condition when the compared results match with each other, and
    the communication section is configured to transmit the determination results indicating the match with the first physiological condition and the measurement result signal so as to be associated with each other when the measurement result matches with the first physiological condition.

3. The sensor device according to claim 1, further comprising:
    a second biological information sensor configured to measure a second biological information as biological information other than the first biological information of the user,
    wherein the processor is configured to analyze the measured second biological information and to determine that the measurement result matches with a second physiological condition.

4. The sensor device configured to be attached to the user according to claim 1,
    wherein the processor is further configured to determine that the measurement result of the first biological information sensor matches a third physiological condition, wherein when the measurement result is determined to match the third physiological condition, the processor is configured to provide the determination result that indicates a match with the third physiological condition to the communication section.

5. A monitoring system comprising:
    the sensor device according to claim 1;
    the plurality of communication devices, individual ones of the plurality of communication devices configured to receive the determination result indicating the match with at least the first physiological condition and identification information of the user from the communication section, wherein the plurality of communication devices are evenly spaced apart, and wherein the plurality of communication devices are located remotely from the user, wherein the individual ones of the plurality of communication devices include an antenna; and a centralized control device including a control center configured to receive information from at least one of the plurality of communication devices and display the information on a display device.

6. The monitoring system according to claim 5, further comprising a plurality of sensor devices comprising the sensor device, individual ones of the plurality of sensor devices configured to be attached to corresponding ones of a plurality of users, wherein the communication section of the sensor device is in communication with a communication section included in a second sensor device of the plurality of sensor devices attached to a different one of the plurality of users.

7. The monitoring system according to claim 6, wherein the local storage is further configured to include analysis pattern information concerning emergency stored in advance, the processor is configured to compare the measurement result with the analysis pattern information concerning emergency, to generate a signal concerning emergency when the compared results match with each other and to transmit the signal concerning emergency to the communication section, the communication section is configured to transmit at least the signal concerning emergency and identification information of the user to the communication device and the communication section of the second sensor device when receiving the signal concerning emergency, and the communication section of the second sensor device is configured to transfer the signal concerning emergency and identification information of the user received from the communication section of the user to additional users of the plurality of users or communication devices when receiving the signal concerning emergency of the user.

8. The sensor device according to claim 1, wherein the local storage is configured to store at least first information, second information and third information, wherein the communication section is configured to transmit at least the first information, the second information and the third information to a communication device of communication devices, wherein the first information includes identification information of the user, wherein the second information includes the first physiological condition, wherein the second information further includes information used for comparison by the processor, wherein the third information includes actual measurement results, determination results determined by the processor and measurement result signals generated by the first biological sensor, and wherein the communication section is configured to hold at least the first information, the second information, and the third information until the communication device becomes communicable.

9. The sensor device according to claim 1, wherein the storage is configured to store at least first information, second information and third information, wherein the communication section is configured to transmit at least the first information, the second information and the third information to a communication device of the communication devices, wherein the first information includes identification information of the user, wherein the second information includes the first physiological condition, wherein the second information further includes information used for comparison by the processor, wherein the third information includes actual measurement results, determination results determined by the processor including an analyzer and measurement result signals generated by the first biological information sensor, wherein the communication section is configured to hold at least the first information, the second information, and the third information until the communication device becomes communicable, wherein the communication section is configured to transmit the first information and the determination results in the third information stored in the local storage only when it is determined that the determination results in the third information matches the first physiological condition.

10. The monitoring system according to claim 5, wherein the plurality of communication devices is configured to use a multi-hop sensor network.

11. The sensor device according to claim 1, wherein the processor is further configured to control the communication section to transmit the determination result and the identification information of the user to the nearest one of the plurality of communication devices in communication with the sensor device only responsive to the determination result indicating the match with the first physiological condition.

\* \* \* \* \*